United States Patent [19]

Wong et al.

[11] Patent Number: 4,932,961
[45] Date of Patent: Jun. 12, 1990

[54] SURGICAL NEEDLE CONFIGURATION WITH FIVE-SIDED CROSS-SECTION

[75] Inventors: John Wong, Bridgewater, N.J.; Thomas D. Maurer, San Angelo, Tex.; Robert Brown, Edinburgh, Scotland; Robert J. Baker, Hampton, N.J.

[73] Assignee: Ethicon, Inc., Somerville, N.J.

[21] Appl. No.: 408,011

[22] Filed: Sep. 15, 1989

[51] Int. Cl.$^5$ .............................................. A61B 17/06
[52] U.S. Cl. ..................................................... 606/223
[58] Field of Search ............................... 606/223, 222

[56] References Cited

U.S. PATENT DOCUMENTS

| | | | |
|---|---|---|---|
| 1,599,059 | 9/1926 | Morton | 606/223 |
| 3,038,475 | 6/1962 | Orcutt | 606/223 |
| 3,238,942 | 3/1966 | Lincoff | 606/223 |
| 4,513,747 | 4/1985 | Smith | 606/223 |
| 4,524,771 | 6/1985 | McGregor et al. | 606/223 |
| 4,799,484 | 1/1989 | Smith et al. | 606/223 |

Primary Examiner—Edward M. Coven
Assistant Examiner—Gary Jackson
Attorney, Agent, or Firm—Paul A. Coletti

[57] ABSTRACT

A needle having three fluted edges, all of the same angular size. The needle presents a five sided cross-section at a tapered end. This results in easier tissue penetration, reduced cross-sectional needle area, better wound opening area performance, and minimized tissue distortion.

4 Claims, 1 Drawing Sheet

111
SURGICAL NEEDLE CONFIGURATION WITH FIVE-SIDED CROSS-SECTION

FIELD OF THE INVENTION

The present invention relates generally to improved surgical needles. More specifically, the present invention relates to surgical needles which have improved sharpness and reduced penetration resistance between needle and tissue during surgery. Most specifically, the present invention relates to a surgical needle whereby the wound opening area is reduced in order to better perform sensitive surgeries by minimizing tissue distortion and improving tissue apposition.

BACKGROUND OF THE INVENTION

The performance criteria of surgical needles can be measured in three interrelated ways. First, needle sharpness is necessary to reduce penetration resistance between needle and tissue. Greater sharpness lessens the external force required to embed the needle into tissue during surgery. Second, it is desirable to improve the needle cross-section so that the tissue opening, more commonly referred to as the wound opening site, is also reduced. As suspected, with improved penetration, the wound opening is also reduced. Third, when wound opening size is reduced, this will generally minimize the amount of tissue distortion during penetration of the needle.

With improved penetration, reduced wound opening and minimized tissue distortion, tissue apposition is generally improved. As a result, finer and more approximate surgery is possible. Thus, with improved needle sharpness, it is increasingly possible to perform more specialized surgery, especially in such highly refined areas as ophthalmology, microsurgery or plastic surgery.

Generally, it has been found that the optimal needle point must have a sharply tapered end, as well as a reduced cross-section. With a sharply tapered end, it is possible to achieve penetration without maximum tissue distortion. The reduced cross-section in this case will also reduce the wound opening area. It has been found that needles triangular in cross-section have performed quite well in conjunction with tapered ends.

Nevertheless, even these triangular needles require refining in order to improve the previously stated needle sharpness criteria. That is, none of the generally triangular needles have acceptably improved all the criteria in order to configure an optimal needle. Triangular shaped cross-section needles usually sacrifice one criterion for an increased benefit in another criterion.

What is needed, therefore, is a needle with improved sharpness which also reduces penetration resistance, as well as reducing wound opening area and minimizing tissue distortion. With this optimized needle cross-section, improved tissue apposition is possible, and highly refined surgery is generally more likely.

SUMMARY OF THE INVENTION

Accordingly, it is an object of the present invention to provide a needle with a tapered cutting edge having a reduced cross-sectional area for improved penetration.

It is further an object of the present invention to provide a surgical needle with a tapered cutting edge having an easy to form cutting edge which results in improved penetration and smaller wound opening.

Finally, it is an object of the present invention to Provide a needle which has edges containing surfaces which can be polished to improve their sharpness.

These and other objects of the present invention are accomplished in a surgical needle having a tapered cutting edge and containing a five-sided cross-section. The cross-section is generally comprised of a flat upper surface which forms a first side of the needle. The first side contains two ends and each first side forms an angular first and second fluted edge. The fluted edges comprise the second and third side of the needle and generally approach each other angularly along opposite sides of the first flat upper surface. On the pair of fluted edges, an indentation is formed along the cross-section so that the first and second fluted edges angularly form fourth and fifth sides which create a third fluted edge.

Thus, the present invention, containing three fluted edges as well as an indented cross-section results in a reduced cross-sectional area with edges which are easy to sharpen, and, therefore, optimize penetration into tissue. This present invention will more readily be understood by the accompanying description of the drawings and the detailed description of the invention, in which:

DETAILED DESCRIPTION OF THE DRAWINGS

DETAILED DESCRIPTION OF THE INVENTION

Figure 6:
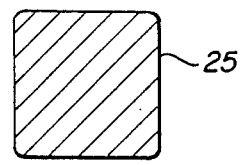
FIG. 6 is a cross-sectional view of a needle of the present invention taken along lines 6—6 of FIG. 3.
Figure 7:
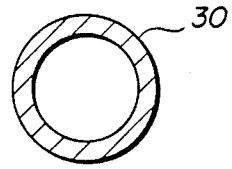
FIG. 7 is a cross-sectional view of a needle of the present invention taken along lines 7—7 of FIG. 3.

As can be seen from FIGS. 1-4, the needle 10 of the present invention is generally curved and has a tapered end 11. The needle has a double concave shape with a radius R about its inner or lower surface 13 and a radius R' about its outer or upper surface 12. The needle begins as a hollow form 30 as can be seen in FIG. 7 and undergoes a transition to a form 25 as can be seen in FIG. 6. This rectangular cross-section 25 increases the strength of the needle, while the hollow end 30 makes the needle light and allows suture attachment.

Figure 1:
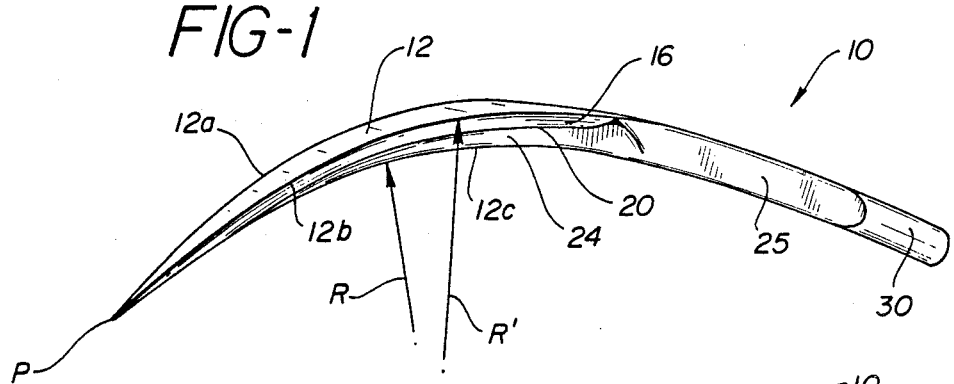
FIG. 1 is a perspective view of a surgical needle of the present invention having an improved cross-sectional design.
Figure 2:
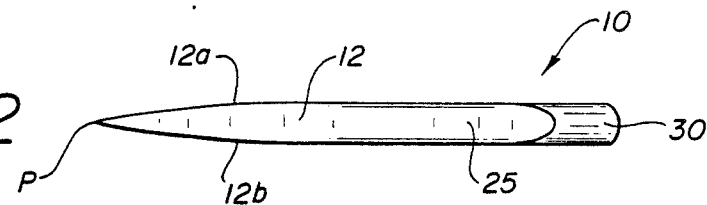
FIG. 2 is a top view of a needle of the present invention.
Figure 3:
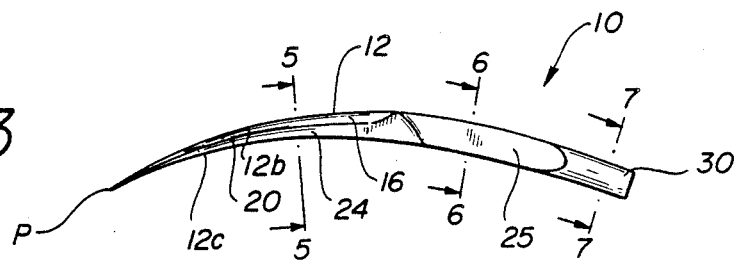
FIG. 3 is a side view of a needle of the present invention.
Figure 4:
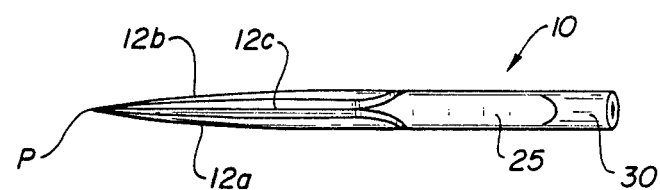
FIG. 4 is a bottom view of a needle of the present invention.
Figure 5:
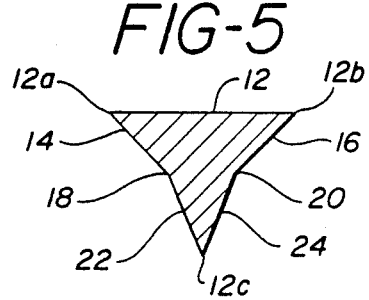
FIG. 5 is a cross-sectional view of a needle of the present invention taken along lines 5—5 of FIG. 3.

As its tapered end 11, the needle 10 has a generally five sided cross-section, as can be seen from FIG. 5. As in FIG. 5, upper surface 12 forms the first side of the cross-section. This upper surface 12 contains ends 12a, 12b. The ends 12a, 12b help form second and third sides 14, 16 which comprise a pair of fluted edges. Each of these sides 14, 16 approach one another on the underside of the upper or outer surface 12.

About midway from the beginning of the upper surface 12, the fluted edges 14, 16 undergo angular changes at indentations 18, 20. These indentations help form fourth and fifth sides 22, 24 as continuations of second and third sides 14, 16. The fourth and fifth sides 22, 24 help form a third fluted edge culminating at needle edge 12c.

The exact size and curvature of the needle is, of course, a matter of choice. Generally, the needle will be formed from a strengthened alloy and have a thickness (diameter) anywhere from 0.004 inches to 0.061 inches. The radius of curvature will generally be anywhere from 0.050 inches to about 6 inches. The length of the arc will be anywhere, depending on choice, from ⅜ to ½ of a circle. By choice, naturally, some needles will remain straight. In all cases, the point P should be as sharp as possible, generally between 1° and 40°.

Most important, however, are the angles formed by the fluted edges. In the present configuration, it is desired to have edges 12a, 12b, 12c having angular cross-sections of about 45°. Naturally, these edges may be further refined or widened anywhere from 5° to 80°, although 45° or less has been found to be most optimal. The 45° angle results in a penetration roughly 15%-20% better than existing needles. Importantly, at these angles, sharpness of the needle can be improved by various known polishing techniques.

In order to create the third fluted edge 12c, it is necessary to create an indentation at 18, 20 and sides 22, 24, which have a cross-sectional included angle from about 30° to about 90°. Generally, it is desired that these indentations be formed such that the included angle in the cross-section is equal. Generally, the indentations 18, 20 will have a cross-sectional included angle between about 190° to about 240°.

Thus, with the improved fluted edges in the present design, the objectives are accomplished. Tissue penetration is performed more readily. Wound opening area is reduced, due to the indented cross-section of the tapered needle end 11 and the sharper edge 12a, 12b, 12c. Finally, tissue distortion is minimized, and improved tissue apposition is available.

While the present invention has been described in conjunction with a particular preferred embodiment, it should be understood that the invention should be determined from the following claims in their equivalents in which:

What is claimed is:

1. A surgical needle having a tapered cutting edge with a five-sided cross-section, said cross-section comprising:
   a flat upper surface forming a first side and having two ends, each said upper surface end forming a first and second fluted edge;
   the fluted edges being the second and third sides and approaching each other opposite said flat upper surface, said fluted edges having equal lengths;
   said fluted edges each ending at an angular connection to the fourth and fifth sides, said fourth and fifth sides angularly connected to form a third fluted edge;
   such that there is an indentation along said needle cross-section formed at both said first and third fluted edges and said second and third fluted edges.

2. The surgical needle of claim 1 wherein the cross-sectional angles of said first, second and third fluted edges are all 45°.

3. The surgical needle of claim 2 wherein the cross sectional angles between said first and third fluted edges and said second and third fluted edges are equal and fall in the range from about 190° to about 240°.

4. The surgical needle of claim 3 wherein said needle forms a double concave surface with said upper surface enclosing said third fluted edge.

* * * * *